United States Patent
Ham et al.

(10) Patent No.: US 10,781,217 B2
(45) Date of Patent: Sep. 22, 2020

(54) IMIDAZOPYRIDAZINE COMPOUND

(71) Applicant: HANMI PHARMACEUTICAL CO., LTD., Hwaseong-si, Gyeonggi-do (KR)

(72) Inventors: Young Jin Ham, Hwaseong-si (KR); Seok Jong Kang, Hwaseong-si (KR)

(73) Assignee: HANMI PHARMACEUTICAL CO., LTD., Hwaseong-si (KR)

(*) Notice: Subject to any disclaimer, the term of this patent is extended or adjusted under 35 U.S.C. 154(b) by 0 days.

(21) Appl. No.: 16/480,758

(22) PCT Filed: Jan. 23, 2018

(86) PCT No.: PCT/KR2018/000982
§ 371 (c)(1),
(2) Date: Jul. 25, 2019

(87) PCT Pub. No.: WO2018/139825
PCT Pub. Date: Aug. 2, 2018

(65) Prior Publication Data
US 2019/0389872 A1 Dec. 26, 2019

(30) Foreign Application Priority Data
Jan. 26, 2017 (KR) .................. 10-2017-0012767

(51) Int. Cl.
*C07D 487/22* (2006.01)
(52) U.S. Cl.
CPC ........ *C07D 487/22* (2013.01); *C07B 2200/07* (2013.01)
(58) Field of Classification Search
CPC .................................................. C07D 487/22
See application file for complete search history.

(56) References Cited

U.S. PATENT DOCUMENTS

2016/0024114 A1   1/2016   Blom et al.

FOREIGN PATENT DOCUMENTS

| KR | 10-2015-0133765 A | 11/2015 |
| WO | 02/066481 A1 | 8/2002 |
| WO | 2010/009155 A2 | 1/2010 |
| WO | 2016146651 A1 | 9/2016 |

OTHER PUBLICATIONS

Pinedo et al. (2000).*
McMahon et al. (2000).*
Babu et al., "Identification of Novel CDK2 Inhibitors by QSAR and Virtual Screening Procedures", QSAR and Combinational Science, vol. 27, Nos. 11-12, pp. 1362-1373 (2008).
Byth et al., "Imidazo[1,2-b]pyridazines: a potent and selective class of cyclin-dependent kinase inhibitors", Bioorganic & Medicinal Chemistry Letters, vol. 14, No. 9, pp. 2249-2252 (2004).
Melnikova et al., "Targeting protein kinases", Nature Reviews, vol. 3, pp. 993-994, Dec. 2004.
Manning et al., "The Protein Kinase Complement of the Human Genome", Science, vol. 298, pp. 1912-1916 and 1933-1934, Dec. 2002 (8 pages total).
Kaelin Jr, et al., "The Concept of Synthetic Lethality in the Context of Anticancer Therapy", Nature Reviews, vol. 5, pp. 689-698, Sep. 2005.
International Searching Authority International Search Report dated Jun. 27, 2018 in PCT/KR2018/000982.

* cited by examiner

*Primary Examiner* — Paul V Ward
(74) *Attorney, Agent, or Firm* — Sughrue Mion, PLLC

(57) ABSTRACT

The present invention relates to an imidazopyridazine compound having cell growth inhibitory activity, and a pharmaceutical composition for preventing or treating cancer or a tumor including the same. The imidazopyridazine compound of Chemical Formula 1 according to the present invention has excellent cell growth inhibitory activity, and thus can be favorably used as a preventive or therapeutic agent for cancer or a tumor.

13 Claims, No Drawings

IMIDAZOPYRIDAZINE COMPOUND

CROSS REFERENCE TO RELATED APPLICATIONS

This application is a National Stage of International Application No. PCT/KR2018/000982 filed Jan. 23, 2018, claiming priority based on Korean Patent Application No. 10-2017-0012767 filed Jan. 26, 2017.

TECHNICAL FIELD

The present invention relates to an imidazopyridazine compound and a use thereof, and in particular, to an imidazopyridazine compound having cell growth inhibitory activity, and a pharmaceutical composition for preventing or treating cancer or a tumor including the same.

BACKGROUND ART

Kinase mediates a reaction of transferring a high energy molecule, particularly a phosphate group of ATP, to a substrate. Kinase performs a role of stabilizing a phosphoric anhydride bond, and increasing a reaction rate by positioning the substrate and the phosphate group at a specific position. In most cases, a transition state obtained by an interaction with a negatively-charged phosphate group is electrostatically stabilized through positively-charged surrounding amino acids, and some kinase forms a coordinate bond with the phosphate group using a metal cofactor.

Kinase may be divided into various groups such as protein kinase, lipid kinase or carbohydrate kinase depending on the substrate and characteristics. Protein, lipid or carbohydrate may vary in the activity, reactivity, and ability to bond to other molecules depending on the phosphorylation state. Kinase widely affects intracellular signal transduction, and regulates complex biological mechanisms within the cell. Some molecules have their activity strengthened or inhibited through phosphorylation, and their abilities to interact with other molecules may be regulated. Since many kinases respond to environmental conditions or signals, a cell may control molecules in the cell through kinase depending on circumstances. Accordingly, kinase performs a very crucial role in cell growth, differentiation, proliferation, survival, metabolism, signal transduction, cell transport, secretion and many other cell reaction pathways.

Kinase has been found in a variety of species ranging from bacteria to fungi, insects and mammals, and more than 500 kinases have been found in humans to date.

Protein Kinase either increases or decreases activity of a protein, stabilizes or becomes a marker for degrading a protein, places a protein in a specific cell compartment, or initiate or disturb interactions with other proteins. Protein kinase is known to occupy the majority of all kinases, and has been an important subject of researches. With phosphatase, protein kinase performs a role of regulating a protein and an enzyme as well as cell signal transduction. A cell protein is a target of numerous covalent bonds, however, since there are not many reversible covalent bonds like a phosphorylation reaction, protein phosphorylation is explained to have a regulatory function. Protein kinase often has multiple substrates, and sometimes a particular protein functions as a substrate for one or more kinases. For this reason, protein kinase is named using a factor regulating its own activity. For example, calmodulin-dependent protein kinase is regulated by calmodulin. Kinase is sometimes divided into subgroups. For example, type 1 and type 2 cyclic AMP-dependent protein kinase is formed with the same enzyme subunits, but is regulated by other regulating subunits binding to the cyclic AMP.

Protein kinase is an enzyme catalyzing phosphorylation of a hydroxy group located on tyrosine, serine and threonine residues of a protein, and performs an important role in transducing a growth factor signal inducing cell growth, differentiation and proliferation (Irena Melnikova and James Golden, *Nature Reviews Drug Discovery* 3, 993, 2004), and abnormal expression or mutation of specific kinase has been reported to be frequent in cancer cells.

Human protein kinase is estimated to have 518 species present corresponding to approximately 1.7% of total human genes (Manning et al, Science, 2002, 298, 1912), and is largely divided into tyrosine protein kinase (90 species or more) and serine/threonine protein kinase. Tyrosine protein kinase may be divided into 58 species of receptor tyrosine kinases divided by 20 subtypes and 32 species of cytoplasm/non-receptor divided by 10 subtypes, and tyrosine kinase (TK) is one type of enzyme transferring one phosphate group from ATP to a hydroxyphenyl group of tyrosine. Tyrosine kinases clearly perform an important role in normal cell growth, which directly participates in a cell signal transduction process.

As one of general methods for a cell to recognize external stimuli, recognition through tyrosine kinase, a receptor present in a cell membrane, is known. Receptor tyrosine kinase (RTK) is formed with an extracellular portion exposed outside the cell, an intracellular portion exposed to cytoplasm inside the cell, and a membrane passing portion passing through a plasma membrane located in the middle. The extracellular portion of the receptor is a part where a specific ligand binds, and the intracellular portion performs a role of transducing active signals of the receptor activated by the ligand into the cell. In the receptor tyrosine kinase, a domain having tyrosine kinase activity in a C-terminal region exposed in the cell is present, and when a specific ligand attaches to the extracellular portion, kinase enzyme of the tyrosine kinase domain at the C-terminal exposed to the cytoplasmic portion of the receptor protein is activated phosphorylating tyrosine at the C-terminus of each other on the duplex. Such a tyrosine phosphorylation process becomes the most important process transducing signals for extracellular stimuli into the cell. Receptors having tyrosine kinase activity transducing extracellular stimuli into the cell with such a mechanism are widely known. Representative examples thereof may include SRC-1, EGFR, PDGFR, IR, IGFR, c-fms, VEGFR, FGFR and the like.

There are numerous signal transduction systems in the cell, and each of these signal transduction systems is organically connected to each other to regulate cell proliferation, growth, death and the like through forming a complex mechanism (William G. Kaelin Jr, *Nature Reviews Cancer* 5, 689, 2005). Accordingly, when an intracellular regulatory function is out of balance due to genetic or environmental influences, amplification or extinction of abnormal signal transduction appears destroying the signal transduction system (mainly a state in which in-vivo signal transduction continues), which causes various diseases such as cancer, inflammation, metabolic diseases or brain diseases.

PRIOR ART DOCUMENTS

Irena Melnikova and James Golden, *Nature Reviews Drug Discovery* 3, 993, 2004;
Manning et al, Science, 2002, 298, 1912;
William G. Kaelin Jr, *Nature Reviews Cancer* 5, 689, 2005.

DISCLOSURE

Technical Problem

The present invention is directed to providing a novel imidazopyridazine compound having excellent cell growth inhibitory activity.

The present invention is also directed to providing a pharmaceutical composition including the compound as an active ingredient.

The present invention is also directed to providing a pharmaceutical composition for preventing or treating cancer or a tumor including the compound as an active ingredient.

Technical Solution

In view of the above, one embodiment of the present invention provides an imidazopyridazine compound of the following Chemical Formula 1, or an optical isomer thereof:

[Chemical Formula 1]

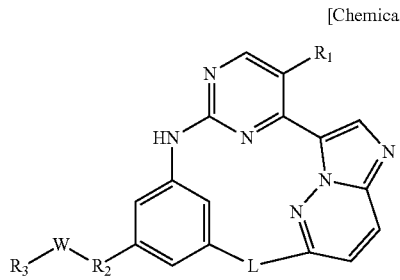

in Chemical Formula 1,
$R_1$ is H or halogen;
L is selected from the group consisting of —CH=CH—, —(CH$_2$)p- and —(CH$_2$)p-O—;
p is an integer of 1 to 3;
$R_2$ is a bond, or —(CH$_2$)n-, —CO—, —NR$_4$—(CH$_2$)n- or —O—(CH$_2$)n-;
n is an integer of 0 to 3;
$R_4$ is H or $C_{1-6}$alkyl;
W is saturated or partially unsaturated 5- to 8-membered unsubstituted or substituted monocyclic heterocycloalkyl or heteroaryl containing 1 to 4 heteroatoms selected from among N, O and S; and
$R_3$ is selected from the group consisting of H, halogen, linear or branched $C_{1-6}$alkyl, linear or branched $C_{2-10}$alkenyl, $C_{3-10}$cycloalkyl, halo$C_{1-5}$alkyl, hydroxy$C_{1-6}$alkyl, amino, mono or di($C_{1-6}$alkyl)amino, hydroxy, $C_{1-6}$alkoxy, $C_{3-10}$cycloalkyl$C_{1-6}$alkyl, (mono or di($C_{1-6}$alkyl)amino)heterocycloalkyl, (hydroxy$C_{1-6}$alkyl)heterocycloalkyl, heterocycloalkyl and hydroxyheterocycloalkyl.

Another embodiment of the present invention provides a pharmaceutical composition and a pharmaceutical formulation including the compound as an active ingredient.

Advantageous Effects

An imidazopyridazine compound of Chemical Formula 1 according to the present invention is capable of exhibiting cell growth inhibitory activity, and therefore, is useful as an agent for preventing or treating cancer or a tumor.

MODE FOR DISCLOSURE

An imidazopyridazine compound of the following Chemical Formula 1, or an optical isomer thereof:

[Chemical Formula 1]

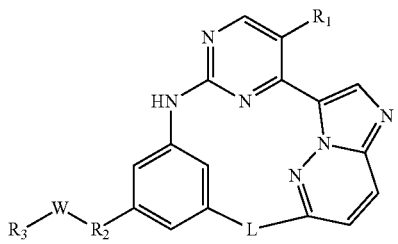

in Chemical Formula 1,
$R_1$ is H or halogen;
L is selected from the group consisting of —CH=CH—, —(CH$_2$)p- and —(CH$_2$)p-O—;
p is an integer of 1 to 3;
$R_2$ is a bond, or —(CH$_2$)n-, —CO—, —NR$_4$—(CH$_2$)n- or —O—(CH$_2$)n-;
n is an integer of 0 to 3;
$R_4$ is H or $C_{1-6}$alkyl;
W is saturated or partially unsaturated 5- to 8-membered unsubstituted or substituted monocyclic heterocycloalkyl or heteroaryl containing 1 to 4 heteroatoms selected from among N, O and S; and
$R_3$ is selected from the group consisting of H, halogen, linear or branched $C_{1-6}$alkyl, linear or branched $C_{2-10}$alkenyl, $C_{3-10}$cycloalkyl, halo$C_{1-5}$alkyl, hydroxy$C_{1-6}$alkyl, amino, mono or di($C_{1-6}$alkyl)amino, hydroxy, $C_{1-6}$alkoxy, $C_{3-10}$cycloalkyl$C_{1-6}$alkyl, (mono or di($C_{1-6}$alkyl)amino)heterocycloalkyl, (hydroxy$C_{1-6}$alkyl)heterocycloalkyl, heterocycloalkyl and hydroxyheterocycloalkyl.

Definitions listed below are definitions of various terms used for describing the present invention. These definitions are used throughout the specification individually or as a part of terms including these unless limited otherwise.

The term 'halogen' used in the present specification means, unless mentioned otherwise, any one of fluorine, chlorine, bromine, iodine, or all of these.

The term 'alkyl' used in the present specification refers to, unless mentioned otherwise, a saturated linear or branched hydrocarbon radical that may be expressed by a chemical formula of $C_nH_{2n+1}$ when having n carbon atoms, and specifically, refers to a saturated linear or branched hydrocarbon radical each including carbon atoms between 1 to 6, 1 to 8, 1 to 10, or 1 to 20. Examples of these radicals include methyl, ethyl, propyl, isopropyl, n-butyl, tert-butyl, neopentyl, n-hexyl, heptyl and octyl radicals, but are not limited thereto.

The term 'alkenyl' used in the present specification refers to, unless mentioned otherwise, a monovalent group derived from unsaturated linear or branched hydrocarbon that has at least one carbon-carbon double bond and may be expressed by a chemical formula of $C_nH_{2n-1}$ when having n carbon atoms, and specifically, refers to an unsaturated linear or branched monovalent group each including carbon atoms between 2 to 6, 2 to 8, 2 to 10, or 2 to 20. Examples thereof include ethenyl, propenyl, butenyl, 1-methyl-2-buten-1-yl, heptenyl and octenyl radicals, but are not limited thereto.

The term 'cycloalkyl' used in the present specification refers to, unless mentioned otherwise, a monovalent hydrocarbon group derived from a monocyclic or polycyclic saturated or unsaturated carbocyclic compound. For example, examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but are not limited to, cyclopropyl, cyclobutyl, cyclopentyl, cyclohexyl, bicyclo [2.2.1]heptyl, and bicyclo[2.2.2]octyl. A monovalent group derived from a monocyclic or polycyclic compound having at least one carbon-carbon double bond obtained by removing a single hydrogen atom is also considered. Examples of such a group include, but are not limited to, cyclopropenyl, cyclobutenyl, cyclopentenyl, cyclohexenyl and cycloheptenyl, cyclooctenyl and the like.

The term 'cycloalkylalkyl' used in the present specification refers to, unless mentioned otherwise, a monovalent hydrocarbon radical in which one or more hydrogens of the alkyl group according to the definition described above are substituted with the cycloalkyl group according to the definition described above. Examples of the $C_{3-10}$cycloalkyl$C_{1-6}$alkyl group include, but are not limited to, cyclopropylmethyl, cyclopropylethyl, cyclohexylmethyl and the like.

The term 'aryl' used in the present specification refers to, unless mentioned otherwise, a mono- or polycyclic hydrocarbon radical having fused or non-fused one or more aromatic rings, and although not limited thereto, includes phenyl, naphthyl, tetrahydronaphthyl, indenyl, idenyl and the like.

The term "heterocyclic radical" used in the present specification includes unsaturated, saturated, aromatic, aliphatic groups and the like such as heteroatom—including cycloalkyl, cycloalkenyl, cycloalkynyl or heteroaryl.

The term 'arylalkyl' used in the present specification refers to, unless mentioned otherwise, a radical in which one or more hydrogens of the alkyl group according to the definition described above are substituted with the aryl group, and although not limited thereto, examples thereof include benzyl, phenethyl and the like.

The term 'heterocycloalkyl' used in the present specification refers to, unless mentioned otherwise, a saturated or partially unsaturated 3-membered to 10-membered mono or polycyclic substituent containing one or more, for example, 1 to 4 heteroatoms selected from among N, O and S. Examples of the monocyclic heterocycloalkyl may include piperidinyl, morpholinyl, thiamorpholinyl, pyrrolidinyl, imidazolidinyl, tetrahydrofuranyl, piperazinyl and groups similar thereto, but are not limited thereto.

The term 'heteroaryl' used in the present specification means, unless mentioned otherwise, a 5-membered to 12-membered mono or polycyclic aromatic monovalent radical containing one or more, for example, 1 to 4 heteroatoms selected from among O, N and S. Examples of the monocyclic heteroaryl may include thiazolyl, oxazolyl, thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl and groups similar thereto, but are not limited thereto. Examples of the bicyclic heteroaryl may include indolyl, benzothiophenyl, benzofuranyl, benzimidazolyl, benzoxazolyl, benzisoxazolyl, benzothiazolyl, benzothiadiazolyl, benzotriazolyl, quinolinyl, isoquinolinyl, furinyl, furopyridinyl and groups similar thereto, but are not limited thereto.

The term 'heteroarylalkyl' used in the present specification refers to, unless mentioned otherwise, a radical in which one or more hydrogens of the alkyl group according to the definition described above are substituted with the heteroaryl group, and although not limited thereto, examples thereof include pyridinylmethyl, pyrimidinylethyl and the like.

In the present specification, expression of the number of carbons used before the name of the functional group, for example, $C_{6-12}$ of the $C_{6-12}$aryl, indicates that the corresponding functional group (aryl) contains the expressed number (6 to 12) of carbon atoms. Such expression of the number of carbons may also be used in presenting one complex functional group obtained by bonding with a plurality of functional groups, and for example, $C_{6-12}$aryl $C_{1-6}$alkyl indicates that one hydrogen of an alkyl group formed with 1 to 6 carbon atoms is substituted with $C_{6-12}$aryl.

Hereinafter, the present invention will be described in more detail.

The present invention relates to an imidazopyridazine compound, and in particular, to an imidazopyridazine compound having cell growth inhibitory activity.

Specifically, the present invention provides an imidazopyridazine compound of the following Chemical Formula 1, or an optical isomer thereof.

[Chemical Formula 1]

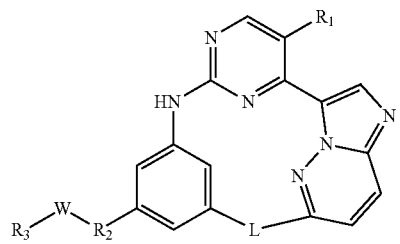

In Chemical Formula 1, $R_1$ is H or halogen;

L is selected from the group consisting of —CH=CH—, —$(CH_2)_p$- and —$(CH_2)_p$-O—;

p is an integer of 1 to 3;

$R_2$ is a bond, or —$(CH_2)_n$-, —CO—, —$NR_4$—$(CH_2)_n$- or —O—$(CH_2)_n$-;

n is an integer of 0 to 3;

$R_4$ is H or $C_{1-6}$alkyl;

W is saturated or partially unsaturated 5- to 8-membered unsubstituted or substituted monocyclic heterocycloalkyl or heteroaryl containing 1 to 4 heteroatoms selected from among N, O and S; and $R_3$ is selected from the group consisting of H, halogen, linear or branched $C_{1-6}$alkyl, linear or branched $C_{2-10}$alkenyl, $C_{3-10}$cycloalkyl, halo$C_{1-5}$alkyl, hydroxy$C_{1-6}$alkyl, amino, mono or di($C_{1-6}$alkyl)amino, hydroxy, $C_{1-6}$alkoxy, $C_{3-10}$cycloalkyl$C_{1-6}$alkyl, (mono or di($C_{1-6}$alkyl)amino)heterocycloalkyl, (hydroxy$C_{1-6}$alkyl)heterocycloalkyl, heterocycloalkyl and hydroxyheterocycloalkyl.

In specific one embodiment of the present invention, L may be —CH=CH— or —$(CH_2)_2$—.

In specific one embodiment of the present invention, $R_1$ may be H or halogen.

In specific one embodiment of the present invention, $R_2$ of Chemical Formula 1 may be —O—$(CH_2)_n$-, and n may be 0, 1 or 2.

In specific one embodiment of the present invention, W may be piperidinyl, piperazinyl, imidazolyl, pyrrolidinyl or morpholine unsubstituted or substituted with one or more types of same or different substituents selected from the group consisting of halogen, cyano, linear or branched $C_{1-6}$alkyl, $C_{3-10}$cycloalkyl, halo$C_{1-5}$alkyl, hydroxy $C_{1-6}$alkyl, amino, mono or di$C_{1-6}$alkylamino, oxo, hydroxy, $C_{1-6}$alkoxy and sulfonyl, but are not limited thereto.

In specific one embodiment of the present invention, the compound of Chemical Formula 1 may be 1-(2-(((1$^5$Z,5Z)-2$^5$-fluoro-3-aza-1(3,6)-imidazo[1,2-b]pyridazina-2(4,2)pyrimidina-4(1,3)-benzenacyclohexapan-5-en-4$^5$-yl)oxy)ethyl)piperidin-4-ol, but is not limited thereto.

Hereinafter, the present invention will be described in more detail with reference to the following preparation examples and examples, however, these are for illustrative purposes only, and the scope of the present invention is not limited thereto.

EXAMPLE

Example 1

1-(2-(((1$^5$Z,5Z)-2$^5$-fluoro-3-aza-1(3,6)-imidazo[1,2-b]pyridazina-2(4,2)pyrimidina-4(1,3)-benzenacyclohexapan-5-en-4$^5$-yl)oxy)ethyl)piperidin-4-ol Step 1) Preparation of 2-amino-3-bromo-5-nitrophenol

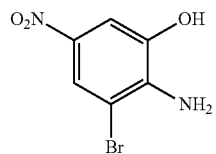 [SMILES: Nc1c(O)cc([N+](=O)[O-])cc1Br]

2-Amino-5-nitrophenol (25 g, 162 mmol) was dissolved in acetonitrile (1.0 L), and N-bromosuccinimide (28.8 g, 170 mmol) was slowly added thereto. The result was stirred for 2 hours at room temperature, and the solvent was removed under vacuum. The result was stirred in a mixed solution of ethyl acetate/hexane (1:1), and produced solids were filtered to obtain a target compound (31.5 g, 83%).

$^1$H-NMR (300 MHz, DMSO-$d_6$): δ 10.66 (s, 1H), 7.83 (s, 1H), 7.46 (s, 1H), 6.15 (s, 2H).

Step 2) Preparation of 3-bromo-5-nitrophenol

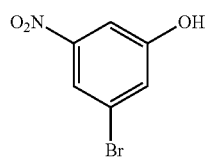 [SMILES: O=[N+]([O-])c1cc(O)cc(Br)c1]

2-Amino-3-bromo-5-nitrophenol (75.6 g, 0.32 mmol) prepared in Step 1) was dissolved in ethanol (1.5 L), and the mixture was cooled to −10° C. Sulfuric acid (62.3 mL, 1.17 mmol) was added thereto over 30 minutes at −10° C. to −2° C. The temperature of the reaction mixture was raised to 50° C. to 55° C., sodium nitrite was slowly added thereto over 30 minutes. The temperature of the reaction mixture was raised to 80° C., and the result was refluxed for 3 hours. After the reaction was completed, the solvent was removed under vacuum, and water and ethyl acetate were added thereto. The organic layer was extracted three times, and washed with salt water. The result was dried with anhydrous sodium sulfate, and concentrated under vacuum. The residue was purified using column chromatography (ethyl acetate:hexane=0.5:10 (v/v)) to obtain a target compound (60 g, 85% yield).

$^1$H-NMR (300 MHz, DMSO-$d_6$): δ 10.90 (s, 1H), 7.75 (s, 1H), 7.51 (s, 1H), 7.36 (s, 1H).

Step 3) Preparation of 3-nitro-5-vinylphenol

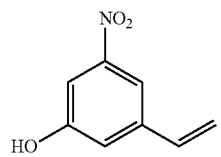

3-Bromo-5-nitrophenol (5 g, 22.93 mmol) prepared in Step 2), potassium vinyltrifluoroborate (9 g, 68.80 mmol), Pd(dppf)Cl$_2$—CH$_2$Cl$_2$ (1.8 g, 2.29 mmol) and triethylamine (9.5 mL, 68.80 mmol) were dissolved in 2-propanol/THF (5:1, 60 mL), and nitrogen was blown thereinto. The reaction mixture was sealed, and, after raising the temperature to 100° C., stirred under reflux for 12 hours. After the reaction was completed, the result was cooled to room temperature, filtered using a filter filled with celite, and washed with ethyl acetate. The organic layer was separated, washed with salt water, and dried with anhydrous sodium sulfate. The solvent was removed under vacuum, and the residue was purified using column chromatography (ethyl acetate:hexane=1:10 (v/v)) to obtain a target compound (3.27 g, 43%).

$^1$H-NMR (300 MHz, CDCl$_3$): δ 7.84 (s, 1H), 7.57 (s, 1H), 7.18 (s, 1H), 6.64 (dd, 1H), 5.82 (d, 1H), 5.41 (d, 1H).

Step 4) Preparation of 1-(2-(3-nitro-5-vinylphenoxy)ethyl)piperidin-4-ol

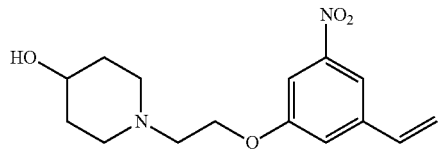 [SMILES: C=Cc1cc(OCCN2CCC(O)CC2)cc([N+](=O)[O-])c1]

3-Nitro-5-vinylphenol (15 g, 83.71 mmol) prepared in Step 3) and 1,2-dibromoethane (8.6 mL, 100.46 mmol) were dissolved in acetonitrile (150 mL), and Cs$_2$CO$_3$ (40.9 g, 125.5 mmol) was added thereto. The reaction mixture was stirred for 12 hours at room temperature. After the reaction was completed, water and ethyl acetate were added thereto. The organic layer was separated, then washed with salt water, dried with anhydrous sodium sulfate, and concentrated under vacuum. The residue was dissolved in DMF (150 mL), and 4-hydroxypiperidine (16.9 g, 167.4 mmol) and potassium carbonate (23.1 g, 167.4 mmol) were added thereto. The reaction mixture was stirred for 2 hours after raising the temperature to 90° C. After the reaction was completed, water and ethyl acetate were added thereto. The organic layer was separated, washed twice with water, washed with salt water, then dried with anhydrous sodium sulfate, and the solvent was removed under vacuum. The residue was purified using column chromatography (dichloromethane:methanol=10:1 (v/v)) to obtain a target compound (15 g, 58% yield).

Step 5) Preparation of 1-(2-(3-amino-5-vinylphenoxy)ethyl)piperidin-4-ol

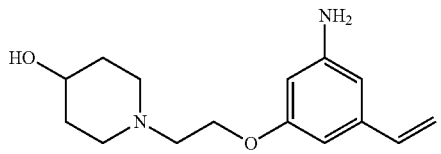 [SMILES: C=Cc1cc(N)cc(OCCN2CCC(O)CC2)c1]

50% ethanol was introduced to iron (Fe powder, 1.59 g, 28.4 mmol), and after slowly adding concentrated hydrochloric acid (conc. HCl, 0.24 mL, 0.27 mmol) thereto, the result was refluxed for 1 hour at 120° C. to be activated. 1-(2-(3-Nitro-5-vinylphenoxy)ethyl)piperidin-4-ol (1.66 g, 5.68 mmol) prepared in Step 4) was added to the activated iron mixture, and the result was refluxed for 1 hour at 120° C. After the reaction was completed, the result was filtered using a filter filled with celite, and to the filtrate, a mixed solution of chloroform/2-propanol (4:1) and a saturated aqueous sodium bicarbonate solution were introduced. The organic layer was separated, then washed with salt water, dried with anhydrous sodium sulfate, and concentrated under vacuum to obtain a target compound (1.2 g, 81% yield).

$^1$H-NMR (300 MHz, CDCl$_3$): δ6.61~6.52 (m, 1H), 6.39 (s, 1H), 6.34 (s, 1H), 6.17~6.16 (m, 1H), 5.69~5.63 (m, 1H), 5.21~5.17 (m, 1H), 4.08~4.04 (t, 2H), 3.71~3.65 (m, 3H), 2.88~2.83 (m, 2H), 2.80~2.76 (t, 2H), 2.31~2.24 (m, 2), 1.93~1.87 (m, 2H), 1.66~1.58 (m, 3H).

Step 6) Preparation of (E)-4-(2-butoxyvinyl)-2-chloro-5-fluoropyrimidine

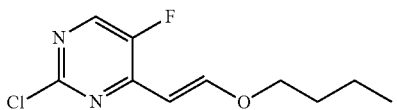

2,4-Dichloropyrimidine (25 g, 149.7 mmol) was introduced to PEG400 (150 mL), and triethylamine (22 mL, 157.2 mmol), butyl vinyl ether (20.4 mL, 157.2 mmol) and palladium acetate (2.36 g, 10.48 mmol) were added thereto. The reaction mixture was stirred for 2 hours at 80° C. After the reaction was completed, the result was cooled to 0° C., and diethyl ether was added thereto. The organic layer was separated, washed three times with water, washed with salt water, then dried with anhydrous magnesium sulfate, and the solvent was removed under vacuum. The residue was purified using column chromatography (n-hexane:ethyl acetate=20:1 (v/v)) to obtain a target compound (13.7 g, 40% yield).

$^1$H-NMR (300 MHz, CDCl$_3$): δ8.20 (m, 1H), 8.00~7.96 (d, 1H), 5.91~5.87 (d, 1H), 4.02~3.98 (t, 2H), 1.77~1.70 (m, 2H), 1.50~1.40 (m, 1H), 0.98~0.93 (t, 3H).

Step 7) Preparation of 6-chloro-3-(2-chloro-5-fluoropyrimidin-4-yl)imidazo[1,2-b]pyridazine

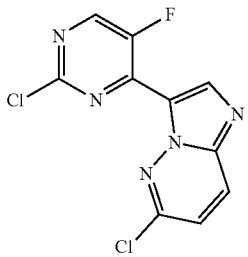 [SMILES: Fc1cnc(Cl)nc1-c1cnc2ccc(Cl)nn12]

(E)-4-(2-butoxyvinyl)-2-chloro-5-fluoropyrimidine (2 g, 8.67 mmol) prepared in Step 6) was dissolved in a mixed solution of 1,4-dioxane/distilled water (3:1, 40 mL), and N-bromosuccinimide (1.54 g, 8.67 mmol) was added thereto. The reaction mixture was stirred for 1 hour at room temperature. After adding 3-amino-6-chloropyridazine (1.12 g, 8.67 mmol) thereto, the reaction mixture was stirred for 2 hours after raising the temperature to 85° C. After the reaction was completed, the result was cooled to room temperature, neutralized (pH=7) by adding a saturated sodium bicarbonate solution thereto, and stirred for 30 minutes at room temperature. Produced solids were filtered and dried to obtain a target compound (1.3 g, 53% yield).

$^1$H-NMR (300 MHz, DMSO-d$_6$): δ9.03 (m, 1H), 8.47 (m, 1H), 8.45~8.41 (d, 1H), 7.66~7.63 (d, 1H).

Step 8) Preparation of 1-(2-(3-((4-(6-chloroimidazo[1,2-b]pyridazin-3-yl)-5-fluoropyrimidin-2-yl)amino)-5-vinylphenoxy)ethyl)piperidin-4-ol

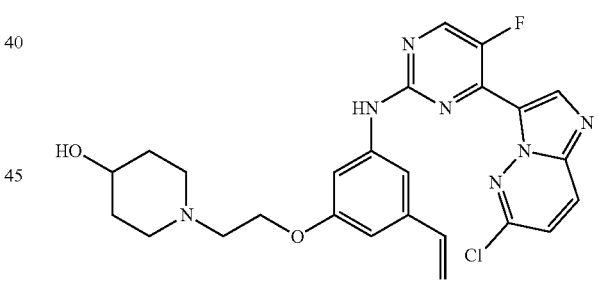

1-(2-(3-Amino-5-vinylphenoxy)ethyl)piperidin-4-ol (260 mg, 0.99 mmol) and 6-chloro-3-(2-chloro-5-fluoropyrimidin-4-yl)imidazo[1,2-b]pyridazine (282 mg, 0.99 mol) prepared in Steps 5) and 7), respectively, were dissolved in 2-butanol, and p-toluenesulfonic acid (p-TsOH; 189 mg, 0.99 mol) was added thereto. The reaction mixture was refluxed for 17 hours at 120° C. After the reaction was completed, the result was cooled to room temperature, and a mixed solution of chloroform/2-propanol (4:1) and a saturated aqueous sodium bicarbonate solution were introduced thereto. The organic layer was separated, then washed with salt water, dried with anhydrous sodium sulfate, and concentrated under vacuum. The obtained residue was purified using column chromatography (CHCl$_3$:MeOH=10:1 (v/v)) to obtain a target compound (185 mg, 37% yield).

$^1$H-NMR (300 MHz, CDCl$_3$): δ8.46 (s, 1H), 8.36 (s, 1H), 8.07~8.04 (d, 1H), 7.40 (m, 1H), 7.29~7.21 (m, 3H), 6.73~6.63 (m, 2H), 5.76~5.70 (d, 1H), 5.27~5.24 (d, 1H), 4.16~4.12 (m, 2H), 3.77~3.72 (m, 1H), 2.90~2.81 (m, 3H), 2.35~2.28 (m, 2H), 1.95~1.90 (m, 2H), 1.69~1.65 (m, 3H).

Step 9) Preparation of 1-(2-(((1⁵Z,5Z)-2⁵-fluoro-3-aza-1(3,6)-imidazo[1,2-b]pyridazina-2(4,2)pyrimidina-4(1,3)-benzenacyclohexapan-5-en-4⁵-yl)oxy)ethyl)piperidin-4-ol

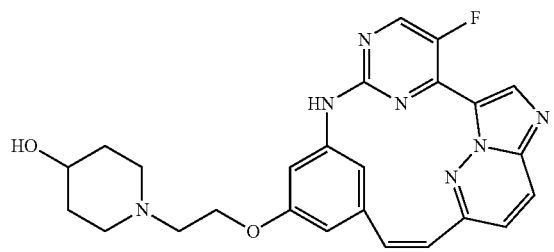 [SMILES: OC1CCN(CCOc2cc3ccc4ccc5ncc(c6nc(ncc6F)[nH]c(c2)c3)n5n4)CC1]

1-(2-(3-((4-(6-Chloroimidazo[1,2-b]pyridazin-3-yl)-5-fluoropyrimidin-2-yl)amino)-5-vinylphenoxy)ethyl)piperidin-4-ol (55 mg, 0.108 mmol) prepared in Step 8) was dissolved in PEG400 (2 mL), and triethylamine (16 μL, 0.113 mmol) and palladium acetate (2 mg, 0.008 mmol) were added thereto. The reaction mixture was stirred for 4 hours at 85° C. After the reaction was completed, the result was cooled to room temperature, water was added thereto, and the result was extracted three times with ethyl acetate. The organic layer was separated, then washed with salt water, dried with anhydrous sodium sulfate, and concentrated under vacuum. The obtained residue was purified using column chromatography (CHCl$_3$:MeOH=10:1 (v/v)) to obtain a target compound (12 mg, 24% yield).

MS: [M+H]$^+$ m/z 473.2;

$^1$H-NMR (300 MHz, DMSO-d$_6$): δ11.14 (bs, 1H), 9.86 (s, 1H), 8.63~8.61 (d, 1H), 8.50~8.49 (d, 1H), 8.31~8.28 (m, 1H), 7.62~7.59 (m, 1H), 6.95~6.90 (m, 1H), 6.75~6.60 (m, 3H), 4.60 (m, 1H), 4.05~4.01 (m, 2H), 2.79~2.71 (m, 2H), 2.67~2.63 (t, 2H), 2.15~2.07 (m, 2H), 1.71~1.67 (m, 2H), 1.39~1.35 (m, 3H).

TEST EXAMPLE

For the compounds prepared in the example, cell growth inhibitory activity results were obtained as follows.

Test Example 1

Evaluation on SK-CO-1 Cell Line

SK-CO-1 cell line purchased from the American Type Culture Collection (ATCC, USA) was cultured at 30° C. with an EMEM medium (10% FBS, 1% penicillin/streptomycin) under the presence of 5% CO$_2$. The cultured SK-CO-1 cell line was prepared in 5×10$^4$/100 μl, placed in a 96 well-plate, and cultured for one day. After that, the test compound was stepwise diluted in a ratio of 1/10 from 10 μM to 0.1 nM in the same EMEM medium, and then cultured for 3 days. In order to measure viability of the cell, a sulforhodamine B colorimetric (SRB, sigma Cat. S1402) test method was used. After discarding the medium, 0.1 ml of 10% trichloroacetic acid (TCA, Sigma Cat. T0699) was introduced to each well, and the cell line was fixed for 30 minutes to 1 hour, then washed with distilled water, and exposed in the air to dry the plate. After that, 100 μl of 0.4% SRB solution was introduced to each well, and the cell line was stained for 30 minutes at room temperature, and the plate was washed with distilled water and 1% acetic acid, and then dried in the air. 150 μl of 10 nM trizma base solution was introduced to each well, and after dissolving the solid SRB therein, absorbance was measured at 540 nM using a microplate-reader. The growth inhibition value (GI$_{50}$) of the cell line was calculated using a GraphPad Prism software. The results are shown in the following Table 1.

TABLE 1

| Cell growth inhibitory activity of imidazopyridazine compound | |
|---|---|
| Compound | GI$_{50}$, nM |
| Example 1 | 21 |

As shown in Table 1, it was seen that the compound of the present invention had excellent cell growth inhibitory activity.

Hereinbefore, the present invention has been described with reference to the examples, however, it is to be understood that these are for illustrative purposes only, and, in the present invention, various modifications and equivalent other examples obvious to those skilled in the art may be implemented within the scope of the appended claims.

The present invention relates to an imidazopyridazine compound and a use thereof, and in particular, to an imidazopyridazine compound having cell growth inhibitory activity, and a pharmaceutical composition for preventing or treating cancer or a tumor including the same.

The invention claimed is:
1. A compound of the following Chemical Formula 1, or an optical isomer thereof:

Chemical Formula 1

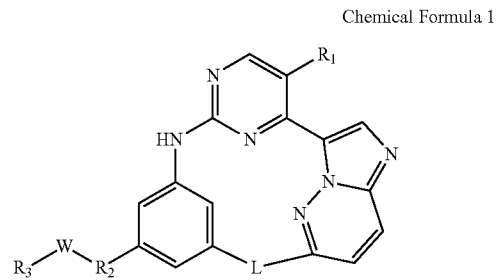

wherein, in Chemical Formula 1,
R$_1$ is H or halogen;
L is selected form the group consisting of —CH=CH—, —(CH$_2$)p- and —(CH$_2$)p-O—;
p is an integer of 1 to 3;
R$_2$ is a bond, or —(CH$_2$)n-, —CO—, —NR$_4$—(CH$_2$)n- or —O—(CH$_2$)n-;
n is an integer of 0 to 3;
R$_4$ is H or C$_{1-6}$alkyl;
W is saturated or partially unsaturated 5- to 8-membered unsubstituted or substituted monocyclic heterocycloalkyl or heteroaryl containing 1 to 4 heteroatoms selected from among N, O and S; and
R$_3$ is selected from the group consisting of H, halogen, linear or branched C$_{1-6}$alkyl, linear or branched C$_{2-10}$alkenyl, C$_{3-10}$cycloalkyl, haloC$_{1-5}$alkyl, hydroxyC$_{1-6}$alkyl, amino, mono or di(C$_{1-6}$alkyl)amino, hydroxy, C$_{1-6}$alkoxy, C$_{3-10}$cycloalkylC$_{1-6}$alkyl, (mono or di(C$_{1-6}$alkyl)amino)heterocycloalkyl, (hydroxyC$_{1-6}$alkyl)heterocycloalkyl, heterocycloalkyl and hydroxyheterocycloalkyl.

2. The compound of Formula 1 according to claim 1, wherein R$_1$ is H or halogen; or an optical isomer thereof.

3. The compound of Formula 1 according to claim 1, wherein L is —CH=CH— or —(CH$_2$)$_2$—; or an optical isomer thereof.

4. The compound of Formula 1 according to claim 1, wherein R$_2$ is —O—(CH$_2$)n-, and n is 0, 1 or 2; or an optical isomer thereof.

5. The compound of Formula 1 according to claim 1, wherein W is a piperidinyl group; or an optical isomer thereof.

6. The compound of Formula 1 according to claim 1, which is 1-(2-(((1$^5$Z,5Z)-2$^5$-fluoro-3-aza-1(3,6)-imidazo[1,2-b]pyridazina-2(4,2)pyrimidina-4(1,3)-benzenacyclohexapan-5-en-4$^5$-yl)oxy)ethyl)piperidin-4-ol; or an optical isomer thereof.

7. A pharmaceutical composition comprising the compound of Formula 1 according to claim 1 or an optical isomer thereof as an active ingredient.

8. A pharmaceutical composition comprising the compound of Formula 1 according to claim 2 or an optical isomer thereof as an active ingredient.

9. A pharmaceutical composition comprising the compound of Formula 1 according to claim 3 or an optical isomer thereof as an active ingredient.

10. A pharmaceutical composition comprising the compound of Formula 1 according to claim 4 or an optical isomer thereof as an active ingredient.

11. A pharmaceutical composition comprising the compound of Formula 1 according to claim 5 or an optical isomer thereof as an active ingredient.

12. A pharmaceutical composition comprising the compound of Formula 1 according to claim 6 or an optical isomer thereof as an active ingredient.

13. A method of treating colorectal cancer comprising administering to a person in need of such treatment a therapeutically effective amount of the compound of Formula I according to claim 1 or an optical isomer thereof.

* * * * *